(12) United States Patent
Yoshimatsu et al.

(10) Patent No.: US 9,384,541 B2
(45) Date of Patent: Jul. 5, 2016

(54) BEAD FILLER INSPECTION APPARATUS, BEAD FILLER INSPECTION PROGRAM AND BEAD FILLER INSPECTION METHOD

(75) Inventors: Keisuke Yoshimatsu, Kodaira (JP); Takahiro Sasaki, Kodaira (JP)

(73) Assignee: BRIDGESTONE CORPORATION, Tokyo (JP)

( * ) Notice: Subject to any disclaimer, the term of this patent is extended or adjusted under 35 U.S.C. 154(b) by 413 days.

(21) Appl. No.: 14/233,182

(22) PCT Filed: Jul. 20, 2012

(86) PCT No.: PCT/JP2012/068517
§ 371 (c)(1),
(2), (4) Date: Jan. 16, 2014

(87) PCT Pub. No.: WO2013/012082
PCT Pub. Date: Jan. 24, 2013

(65) Prior Publication Data
US 2014/0125792 A1    May 8, 2014

(30) Foreign Application Priority Data
Jul. 20, 2011 (JP) .................................. 2011-158921

(51) Int. Cl.
*H04N 7/18* (2006.01)
*G06T 7/00* (2006.01)
(Continued)

(52) U.S. Cl.
CPC .......... *G06T 7/0004* (2013.01); *B29D 30/0061* (2013.01); *B29D 30/48* (2013.01); *G01N 21/8851* (2013.01); *G01N 21/9515* (2013.01);
(Continued)

(58) Field of Classification Search
CPC ............. G06T 7/0004; B29D 30/0681; B29D 2030/481; B29D 30/0061; B29D 30/48; G01M 17/02; G01M 21/8851; G01M 21/9515
USPC .......................................................... 348/86
See application file for complete search history.

(56) References Cited

U.S. PATENT DOCUMENTS

| 2008/0163983 A1* | 7/2008 | Cunningham ........ B60C 25/135 |
| | | 157/1.24 |
| 2011/0011171 A1* | 1/2011 | Nakano .................. B60C 25/00 |
| | | 73/146 |
| 2011/0188731 A1* | 8/2011 | Sekiguchi .............. G01B 11/30 |
| | | 382/141 |

FOREIGN PATENT DOCUMENTS

| JP | A-2007-76289 | 3/2007 |
| JP | A-2008-74329 | 4/2008 |

OTHER PUBLICATIONS

International Search Report issued in International Patent Application No. PCT/JP2012/068517 dated Aug. 28, 2012.

*Primary Examiner* — Allen Wong
(74) *Attorney, Agent, or Firm* — Oliff PLC

(57) ABSTRACT

An imaging device that captures an image of a specific region containing a boundary between an outer edge of the bead filler and a support body; an image processing device that detects an edge corresponding to the boundary between the outer edge of the bead filler and the support body based on an image captured by the imaging device, and that computes distances between a reference model line, that runs along the rotation direction of the support body and is determined based on a detected edge, and each respective point on the edge present in a region containing a join portion; and a control device that performs good/no-good determination on the join portion based on the distances between the reference model line and each of the points on the edge.

5 Claims, 21 Drawing Sheets

(51) Int. Cl.
  *B29D 30/00* (2006.01)
  *G01N 21/88* (2006.01)
  *G01N 21/95* (2006.01)
  *B29D 30/06* (2006.01)
  *B29D 30/48* (2006.01)
  *G01M 17/02* (2006.01)

(52) U.S. Cl.
  CPC ....... *B29D 30/0681* (2013.01); *B29D 2030/481* (2013.01); *G01M 17/02* (2013.01)

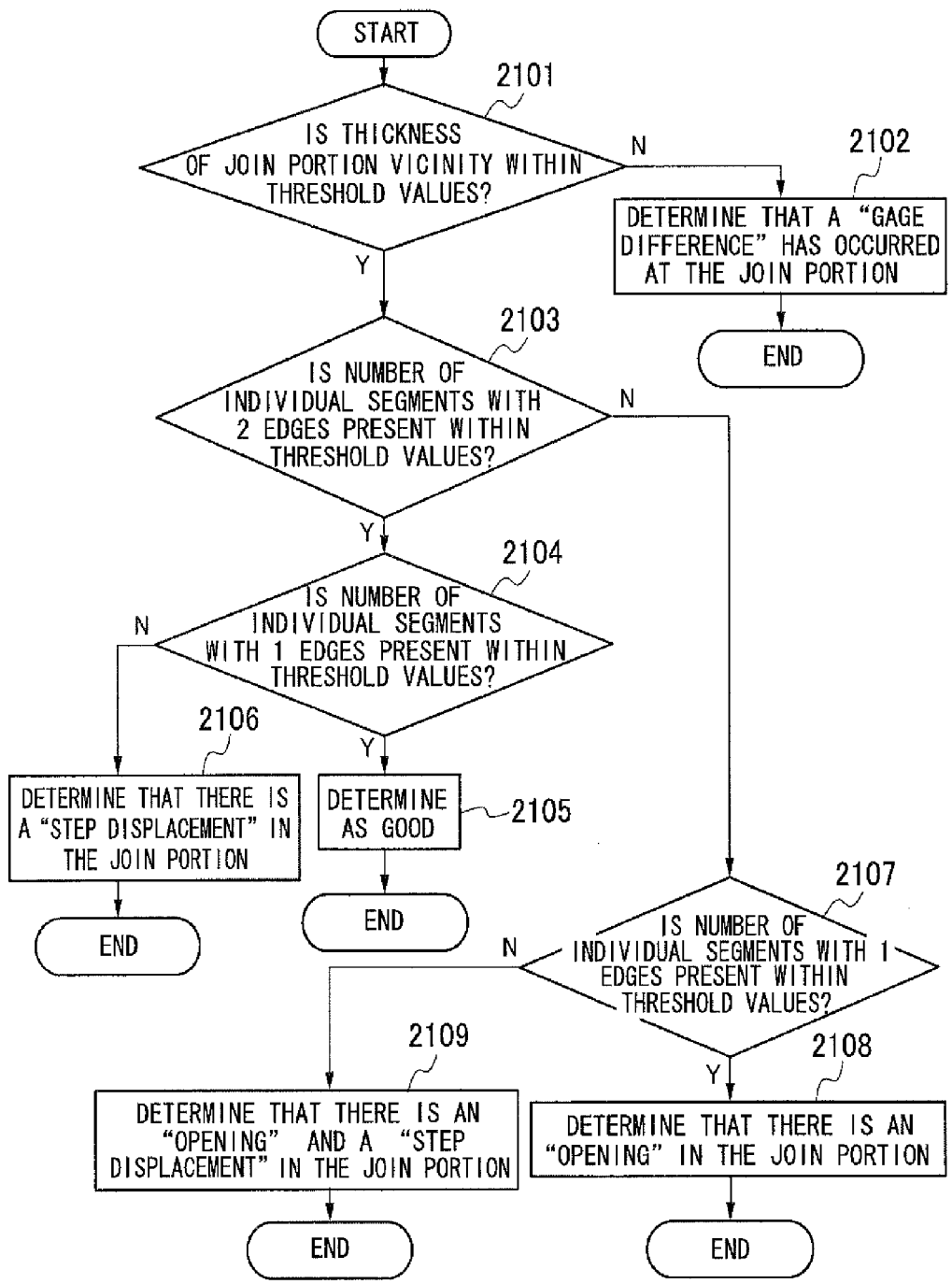

//BEAD FILLER INSPECTION APPARATUS, BEAD FILLER INSPECTION PROGRAM AND BEAD FILLER INSPECTION METHOD

TECHNICAL FIELD

The present invention relates to a bead filler inspection apparatus, a bead filler inspection program and a bead filler inspection method.

BACKGROUND ART

A bead portion that is a portion of a pneumatic tire that makes contact with a tire rim, needs to firmly fix the tire to the rim and so employs as a core a bead core formed by wrapping rubber cover tape on a metal wire formed in a ring shape.

In a configuration with the bead portion described above embedded into a carcass configuring a tire with the bead portion joined to the rim, such a bead core is the portion that transmits motive force of the drive wheels through the rim. The bead portion accordingly needs to have a certain degree of rigidity.

In order to secure rigidity, a flange shaped bead filler is mounted as reinforcement to the bead core, and a carcass is assembled with the bead filler in a mounted state.

In order to mount the bead filler to the bead core, generally a belt shaped member is wrapped around the periphery of the bead core. The bead filler is accordingly not an endless single unit flange, but instead has a join portion 17 at one location, as illustrated in FIG. 2.

The bead filler is designed to reinforce the bead portion of the tire, and so the ends of the member 14 need to accurately join at the join portion 17 without gaps or misalignment.

However, even though the belt shaped member 14 is accurately cut to a specific dimension, since it is made from soft uncured rubber, sometimes the ends of the member 14 do not accurately meet due to the tension force applied to the member 14 during winding, the winding speed and conditions of the operating environment such as the temperature or the humidity, and so there is sometimes misalignment at the join of the ends of the member 14.

FIG. 3 is a diagram illustrating situations of join defects of bead filler. The left hand side of FIG. 3 illustrates a state in which there is "step misalignment" in the top-bottom direction, namely in the width direction of the member between one end of the member 14 and the other end of the member 14 at the join portion of a belt shaped member. The center of FIG. 3 illustrates a state of an "opening" where a gap occurs between ends of the belt shaped member, and a band shaped member is not completely joined. The right hand side of FIG. 3 illustrates a state of a "gage difference" where one end of a belt shaped member rises up and is joined over the other end thereof.

Discovering join portion defects such as those illustrated in FIG. 3 is performed using visual inspection by inspectors, and good/no-good determination of join portions depends on the experience and number of inspectors.

However, due to determination by visual inspection by an inspector involving the subjectivity of the inspector, the existence of different determination standards cannot be discounted, with there being concern regarding variation in good/no-good determination of the join portions depending on the different inspectors. Moreover, the occurrence of determination mistakes cannot be discounted even for a veteran inspector.

Considerable man-hours are also involved in checking, and since all of these man-hours are related to visual confirmation, there is also an issue regarding the large amount of time required for inspection.

Thus a bead inspection device is described in JP-A No. 2007-76289 wherein the entire periphery of a stiffener applied bead (a bead application bead filler) is captured as an inspection target by successive images, and then based on the captured images, a length L1 between a lower end at one side portion of a stiffener (bead filler) joined to the outer peripheral face of a bead and the end at the one side, and a length L2 between a lower end at the other side portion of the stiffener joined to the outer peripheral face of the bead and the end at the other side of the bead, are computed, and determination is made as to whether or not L1 and L2 fall within a permitted range.

Moreover, in JP-A No. 2008-74329 a bead filler inspection device is described that employs a two-dimensional displacement sensor, wherein a laser is illuminated in a line form onto a bead application bead filler, shape deformation of the bead application bead filler is measured from reflected light in the thickness direction (the Z axis direction) of the bead application bead filler, each position of the bead application bead filler is measured in the width direction (the X axis direction), and from these measurement results, two dimensional shape data (a profile) of a cross-section in the Z axis direction is generated for the bead application bead filler. Determination is then made as to whether or not the dimensions of the generated shape data match specific reference values in each of the thickness (Z axis direction) and the width (X axis direction).

SUMMARY OF INVENTION

Technical Problem

However, in the apparatus described in JP-A No. 2007-76289, the length L1 between a lower end at one side portion of a stiffener joined to the outer peripheral face of the bead and the end at the one side, and the length L2 between the lower end at the other side portion of the stiffener joined to the outer peripheral face of the bead and the end at the other side of the bead are computed, and determination is made as to whether or not L1 and L2 fall within a permitted range. Therefore, although detection can be made of "step misalignment" of the one end of a member or the other end of the member at the join portion as illustrated on the left hand side of FIG. 3, there is an issue that an "opening" where a gap has occurred in the join portion of the member as illustrated at the center of FIG. 3, or a "gage difference" that is state in which one end of a member is fixed rising up over the another end of the member as illustrated in FIG. 3, cannot be detected.

In the device described in JP-A No. 2008-74329, the width of a member is measured by employing a two dimensional displaceable sensor for measurement, illuminating a laser onto black rubber member, and onto an uncoated metal support body on which the member is mounted. However, it is difficult to accurately measure the thickness of the bead filler since the laser reflectivity is significantly different between the black rubber and the uncoated metal. Thus particularly when the bead is extremely small, there is an issue that it becomes difficult to discriminate between a projection due to the extremely small bead, and a change in thickness of bead filler related to a defect location such as a "gage difference".

In consideration of the above circumstances, an object of the present invention is to provide a bead filler inspection apparatus, a bead filler inspection program and a bead filler inspection method capable of good/no-good determination of a bead filler join portion even for an extremely small bead.

Solution to Problem

According to a first aspect of the present invention, a bead filler inspection apparatus is provided including: an imaging section that captures an image of a join portion of a bead filler formed by being wound onto a rotating support body and joined, and a region containing a boundary between an outer edge of the bead filler and the support body; an edge detection section that detects an edge corresponding to the boundary between the outer edge of the bead filler and the support body based on an image obtained by the imaging section; a computation section that computes distances between a reference model line, that runs along the rotation direction of the support body and is determined based on an edge detected by the edge detection section, and each respective point on the edge present in a region containing the join portion; a determination section that performs good/no-good determination on the join portion based on the distances.

In the first aspect of the present invention, the distances between a reference model line determined based a detected edge and each respective point on the edge present in the region containing the join portion are computed, enabling good/no-good determination to be performed on the join portion based on the distances. An edge is present that has diverged from the reference model line when the distances are a specific value or greater, enabling the join portion to be determined as no-good. Examples of cases of no-good join portions include "step misalignment", "opening", and "gage difference".

A second aspect of the present invention provides the bead filler inspection apparatus of the first aspect, wherein: the determination section determines that there is an opening in the bead filler join portion when there is a pair of left-right determination target edges present where the distance between the reference model line and each of the respective points on an edge present in the region containing the join portion exceeds a predetermined distance threshold value.

The second aspect of the present invention enables the bead filler join portion to be determined to have an opening when there are a pair of intersection points between extension lines of the determination target edges and the reference model line present.

A third aspect of the present invention provides the bead filler inspection apparatus of the first aspect, wherein: the determination section determines that one end of a member for forming the bead filler is misaligned in a width direction with respect to the other end of the member at the bead filler join portion when the determination target edge and the reference model line do not intersect with each other.

The third aspect of the present invention enables determination that one end of the member is misaligned in a width direction with respect to the other end of the member at the bead filler join portion when the determination target edge and the reference model line do not intersect with each other.

A fourth aspect of the present invention provides a bead filler inspection program that causes a computer to function as: an edge detection section that, based on an image captured by an imaging section that captures an image of a join portion of a bead filler formed by being wound onto a rotating support body and joined and a region containing a boundary between an outer edge of the bead filler and the support body, detects an edge corresponding to the boundary between the outer edge of the bead filler and the support body; a computation section that computes distances between a reference model line, that runs along the rotation direction of the support body and is determined based on an edge detected by the edge detection section, and each respective point on the edge present in a region containing the join portion; a determination section that performs good/no-good determination on the join portion based on the distances.

The fourth aspect of the present invention enables good/no-good determination to be made on the join portion by computing the distances between the reference model line determined based on the detected edge and each respective point on the edge present in the region containing the join portion, and, based on the distances, enables good/no-good determination to be performed on the join portion. The join portion can be determined to be no-good when the distances are a specific value or greater, since an edge is present that deviates from the reference model line. Examples of cases of no-good join portions include "step misalignment", "opening", and "gage difference".

A fifth aspect of the present invention provides a bead filler inspection method that includes: a step for image capturing that captures an image of a join portion of a bead filler formed by being wound onto a rotating support body and joined, and a region containing a boundary between an outer edge of the bead filler and the support body; a step for edge detecting that detects an edge corresponding to the boundary between the outer edge of the bead filler and the support body based on an image obtained by imaging during image capturing; a step for computing that computes distances between a reference model line, that runs along the rotation direction of the support body and is determined based on an edge detected by the edge detecting, and each respective point on the edge present in a region containing the join portion; a step for determining that performs good/no-good determination on the join portion based on the distances.

The fifth aspect of the present invention enables good/no-good determination to be made on the join portion by computing the distances between the reference model line determined based on the detected edge and each respective point on the edge present in the region containing the join portion, and, based on the distances, enables good/no-good determination to be performed on the join portion. The join portion can be determined to be no-good when the distances are a specific value or greater, since an edge is present that deviates from the reference model line. Examples of cases of no-good join portions include "step misalignment", "opening", and "gage difference".

Advantageous Effects of Invention

As explained above, the bead filler inspection apparatus, the bead filler inspection program and the bead filler inspection method of the present invention exhibit the advantageous effect of enabling good/no-good determination to be performed of bead filler join portions even with extremely small beads.

BRIEF DESCRIPTION OF DRAWINGS

FIG. 21 is a flow chart illustrating good/no-good determination of a bead filler join portion according to the second exemplary embodiment of the present invention.

DESCRIPTION OF EMBODIMENTS

First Exemplary Embodiment

Figure 4:
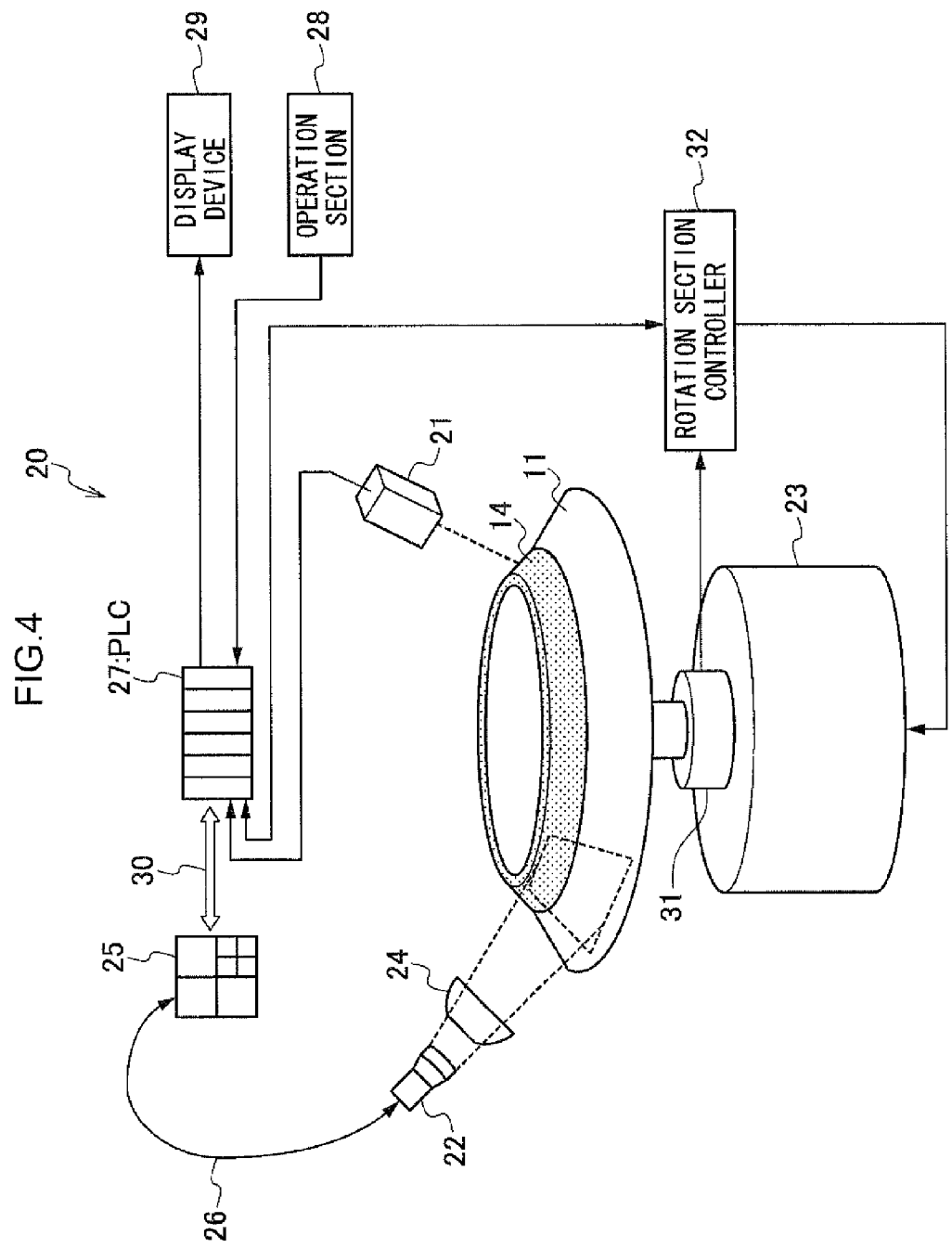
FIG. 4 is a schematic diagram of a bead filler inspection apparatus according to a first exemplary embodiment of the present invention.

Detailed explanation next follows regarding a first exemplary embodiment of the present invention, with reference to the drawings. FIG. 4 is a schematic diagram illustrating a bead filler inspection apparatus according to the first exemplary embodiment of the present invention.

A bead filler inspection apparatus 20 according to the first exemplary embodiment of the present invention illustrated in FIG. 4 includes: a support body 11 of circular conical shape wound with a member 14; a one-dimensional displacement sensor 21 that is a device that illuminates a laser on a specific region containing a join portion of the member 14, for example a region centered on the join portion, that receives reflected light therefrom, and measures the thickness of this region of the member 14; a CCD camera 22 that captures a specific region including the boundary between the join portion of the bead filler and the outer edge of the bead filler, for example a region centered on the join portion of the member 14; a rotation section 23 such as a servomotor that rotates the support body 11 at a certain speed, and that controls so as to stop rotation at a specific position; a light 24 that illuminates the region captured by the CCD camera 22; a camera amplifier 25 that performs image processing on images captured by the CCD camera 22; a camera cable 26 that connects the CCD camera 22 and the camera amplifier 25; a Programmable Logic Controller (PLC) 27 that controls a one-dimensional displacement sensor 21 and the camera amplifier 25 and determines whether or not the join portion of the member 14 is good based on the measurement result of the one-dimensional displacement sensor 21 and the result of image processing by the camera amplifier 25; an operation section 28 for operating the PLC 27; a display device 29 that displays results of good/no-good determination on the join portion of the member 14, based on the measurement result of the one-dimensional displacement sensor 21 and the result of image processing by the camera amplifier 25; and an input-output interface 30 that connects the camera amplifier 25 and the PLC 27.

The operation section 28 is a device for operating the PLC27, such as a keyboard, touch-panel, mouse or pen tablet, and the display device 29 is a device capable of outputting measurement results, such as by display or printing. The input-output interface 30 is an interface that enables inter-device digital communication to be performed, such as ETHERNET (registered trademark), an RS-232 or a CUSB.

A position detector 31 such as a rotation angle sensor, for example a rotary encoder, and a rotation section controller 32 that controls rotation of the rotation section 23, are connected to the rotation section 23.

Based on a command from the PLC 27, the rotation section controller 32 starts rotation of the rotation section 23, and the position detector 31 detects the rotation angle of the rotation section 23 and inputs data of the detected rotation angle of the rotation section 23 after rotation start to the rotation section controller 32.

The rotation angle data is transmitted to the PLC 27 2 via the rotation section controller 32, and employed to detect the position of a join portion 17.

The rotation section controller 32 controls rotation of the rotation section 23 based on instructions from the PLC 27.

Note that a program in the camera amplifier 25 that performs image processing of images captured by the CCD camera 22, a program in the PLC 27 that controls the one-dimensional displacement sensor 21 and the camera amplifier 25, and that performs good/no-good determination on the join portion of the member 14 based on the measurement result of the one-dimensional displacement sensor 21 and the result of image processing by the camera amplifier 25, and a program in the rotation section controller 32 that controls rotation of the rotation section 23, are each stored in respective memories therein.

Explanation next follows regarding an outline of the structure and detection of a bead filler join portion in the first exemplary embodiment of the present invention, with reference to the drawings.

Figure 1:
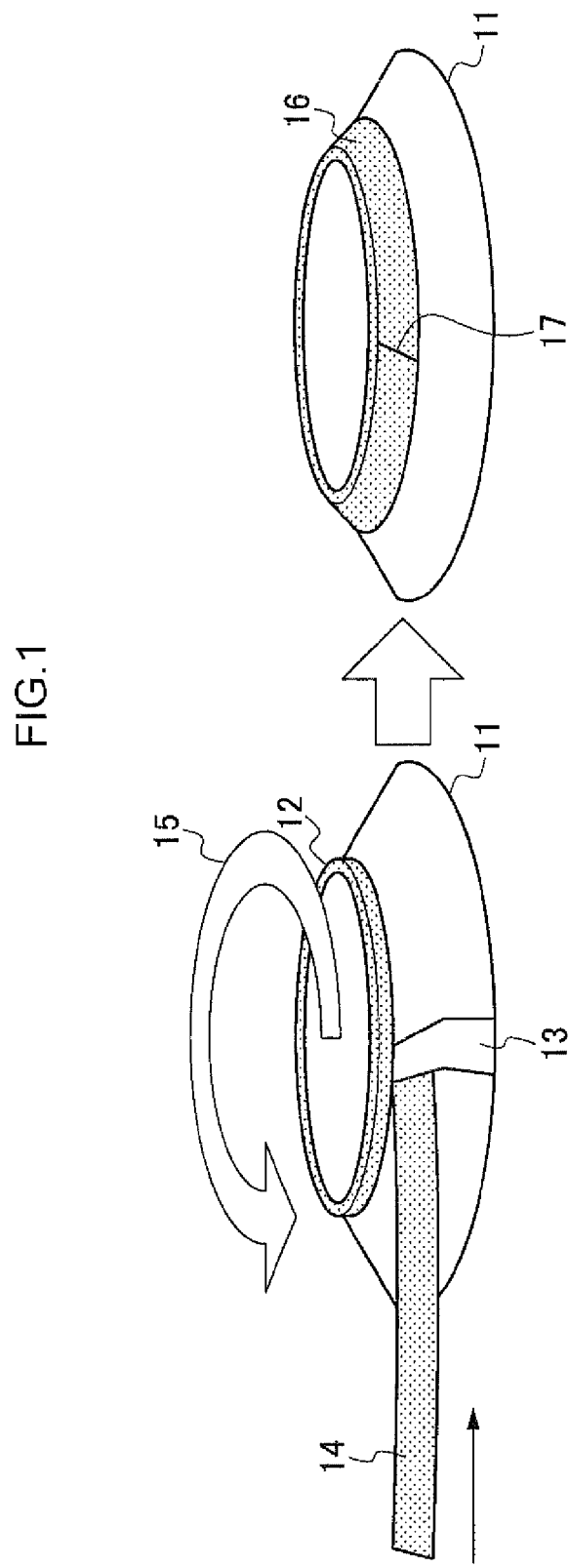
FIG. 1 is a diagram schematically illustrating a process for mounting a bead filler to a bead core.
Figure 2:
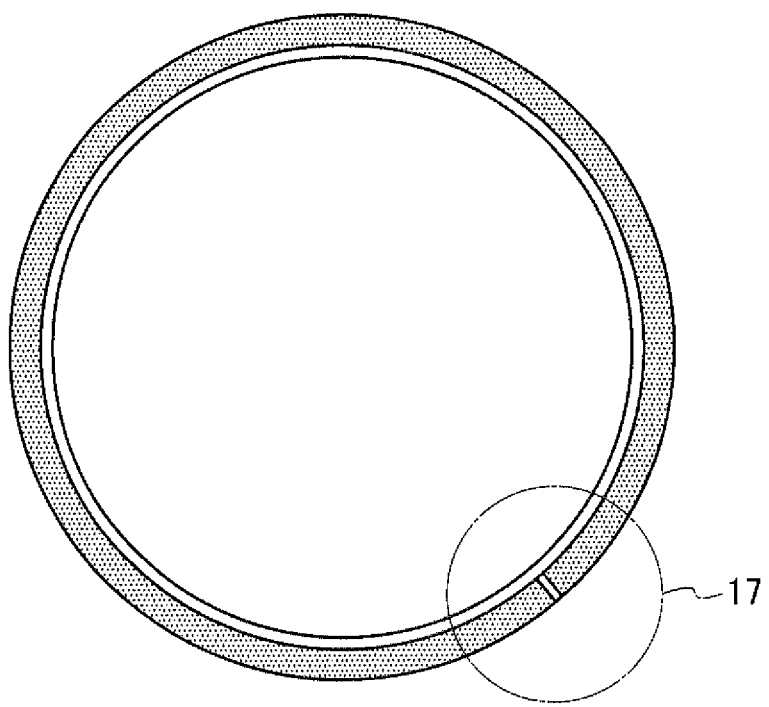
FIG. 2 is a diagram illustrating a join portion of a bead application bead filler.

First, as illustrated in FIG. 1, a belt shaped member 14, that already has uncured rubber formed on the support body 11 set with a bead core 12, is anchored with a fastening 13, the support body 11 is rotated in the rotation direction illustrated by the arrow 15, and the member 14 wound onto the support body 11. The uncured rubber prior to vulcanization processing has adhesive properties, and adheres to the bead core 12 even without employing a separate adhesive, so as to bond the ends of the member 14 together, and to form the bead filler.

Note that joining of the ends of the member 14 of the present exemplary embodiment together may be performed by abutting the ends of the member 14 together in a "butt joint", or by overlapping the ends of the member 14 in a "lap joint". In lap joints, in order to avoid a gage difference arising in the join portion, the ends of the member 14 may be formed in a tapered shape, so that the taper shaped ends of the member 14 are joined together.

Figure 5:
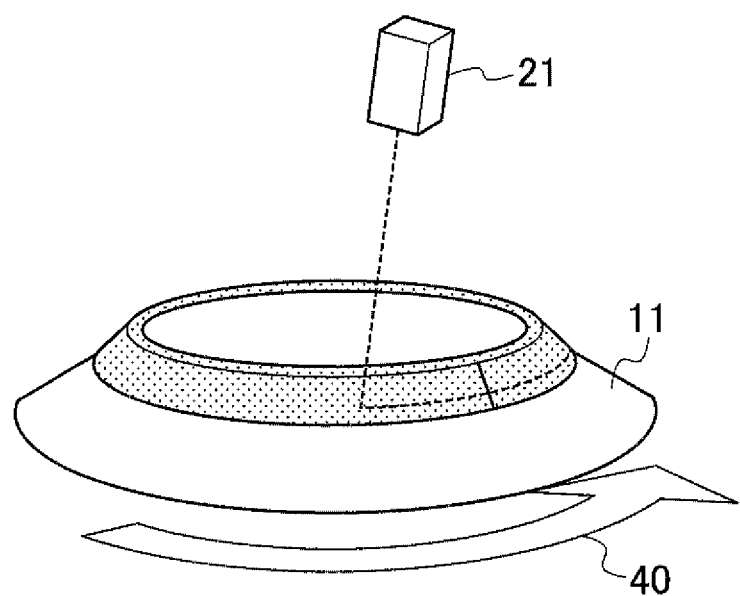
FIG. 5 is a diagram illustrating measurement of a bead filler join portion using a one-dimensional displacement sensor.

Next, as illustrated in FIG. 5, the thickness of the join portion between the ends of the member 14 and the vicinity of the join portion is measured using the one-dimensional displacement sensor 21. When measurement of the join portion and the vicinity of the join portion is performed, this may be achieved by rotating the support body 11 wound with the member 14 in the direction illustrated by arrow 40 whilst the one-dimensional displacement sensor is fixed.

Figure 3:
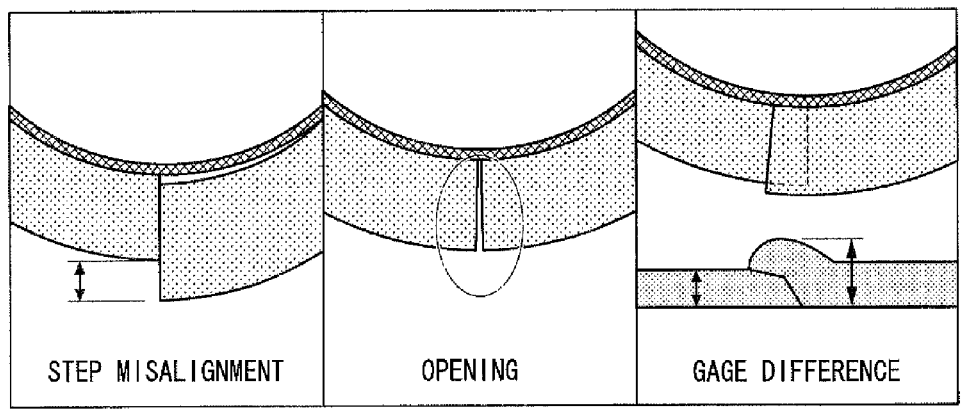
FIG. 3 is a diagram illustrating situations of joint defects of bead filler.

Any locations where the thickness of the join portion measured by the one-dimensional displacement sensor is found to be thicker than other locations may be thought of as arising from "gage difference" as illustrated at the right hand side of FIG. 3. Specifically, "gage difference" can be determined to have occurred at the join portion when the measurement result of the thickness by the one-dimensional displacement sensor exceeds a predetermined threshold value.

In the present exemplary embodiment, the one-dimensional displacement sensor illuminates a spot laser, the laser is not illuminated onto the support body 11 that has a significant different reflectance to the member 14, and the laser is only traced over the member 14. The thickness of the join portion 17 of the member 14 can accordingly be accurately measured without a large difference in reflection of the laser according to the illumination position.

Figure 6:
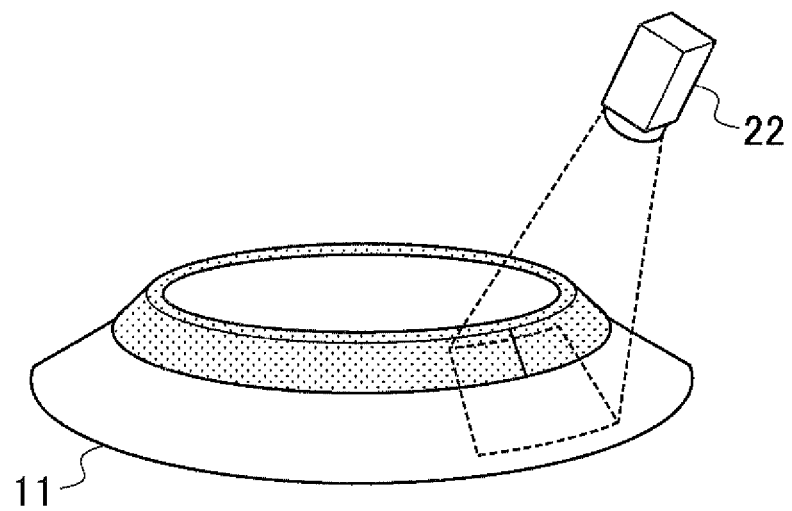
FIG. 6 is a diagram illustrating imaging of a bead filler join portion using a CCD camera.

When measurement by the one-dimensional displacement sensor has been completed, the rotation of the rotation section 23 is halted at a position that enables an image to be captured by the CCD camera 22 of the join portion and the join portion vicinity, and, as illustrated in FIG. 6, an image is captured by the CCD camera 22 of the join portion and the join portion vicinity. The outline portion of the bead filler join portion needs to be captured in the captured image, and so image capture is performed so as to include a region containing the join portion and the join portion vicinity of the bead filler, and a portion of the support body 11 adjacent to this region within a single captured image.

Note that in the present exemplary embodiment, the CCD camera 22 is a monochrome still camera, however a camera that captures color images may be employed, depending on the type of image processing.

Then, image processing is performed of the image captured of the join portion and the join portion vicinity, and an overall determination made of the result of this image processing and the measurement result by the one-dimensional displacement sensor 21, good/no-good determination made of the join portion of the member 14, and the result displayed on the display device 29 of FIG. 4.

Figure 7:
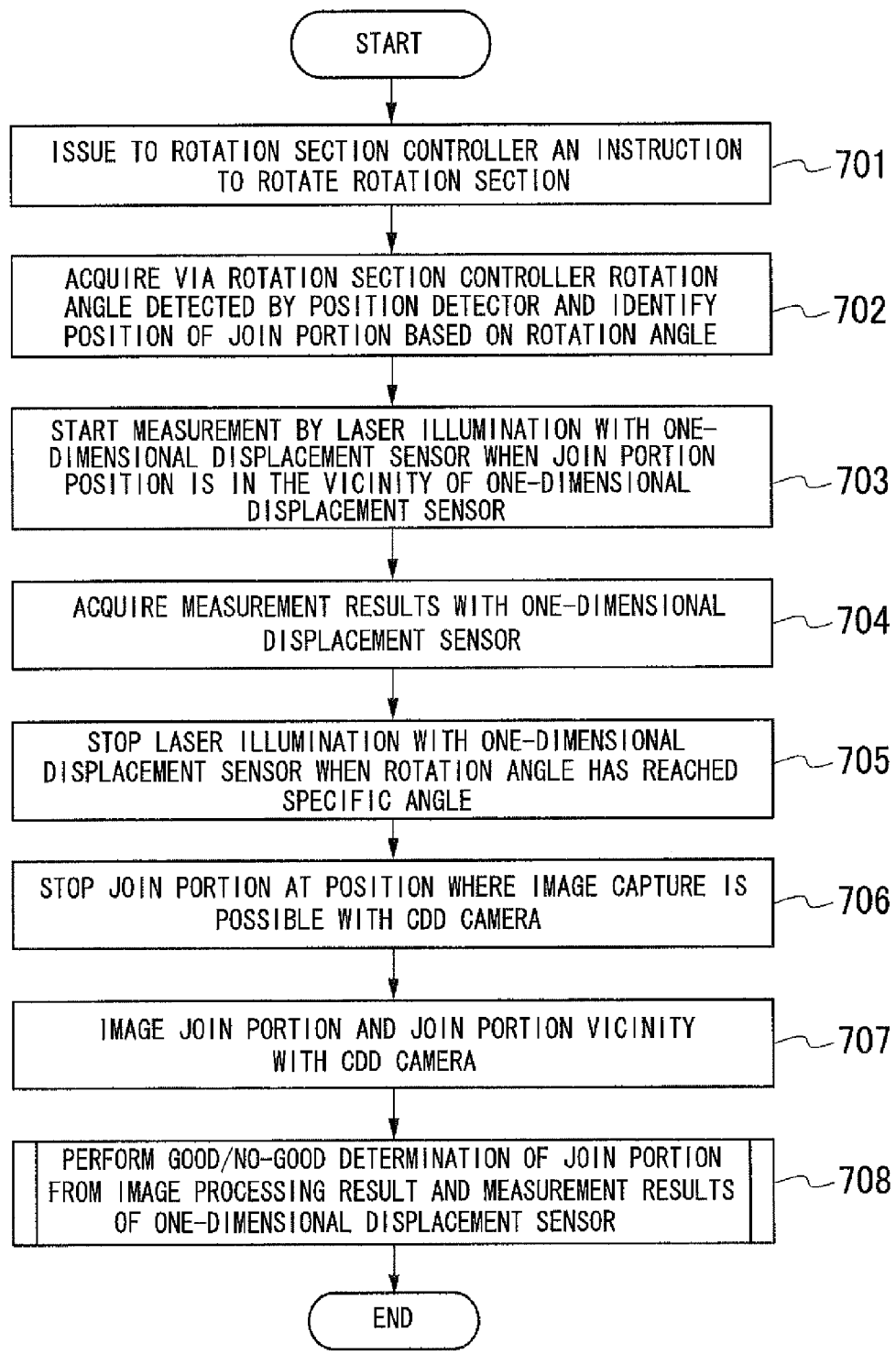
FIG. 7 is a flow chart illustrating a flow of processing in bead filler inspection according to a first exemplary embodiment of the present invention.

Explanation next follows regarding explanation of processing according to a program in bead filler join portion detection of the first exemplary embodiment of the present invention, with reference to FIG. 7. FIG. 7 is a flow chart illustrating a flow of processing of a PLC during bead filler join portion detection of the first exemplary embodiment of the present invention.

Prior to the processing of FIG. 7, the member 14 is wound on the support body 11 that has already been set with the bead core 12, and the rotation section 23 is temporarily stopped with the join portion 17 in a specific position.

First, at step 701, the PLC outputs an instruction to rotate the rotation section 23 to the rotation section controller device 32. According to this instruction, the rotation section controller 32 starts rotation of the rotation section 23.

At the next step 702, the rotation angle detected by the position detector 31 is read through the rotation section controller 32, and the position of the join portion 17 detected based on this rotation angle.

At the next step 703, when the position of the join portion 17 computed based on the rotation angle read through the rotation section controller 32 is determined to have reached the vicinity of the one-dimensional displacement sensor 21, a measurement start command is issued to the one-dimensional displacement sensor 21. With this command as a trigger, the one-dimensional deformation sensor 21 starts measurement of the thickness of the join portion and the join portion vicinity of the member 14 by illuminating the laser onto the join portion and the join portion vicinity whilst gradually moving the join portion and the join portion vicinity to directly under the one-dimensional displacement sensor 21 by rotating the rotation section 23.

At step 704, a measurement result is acquired by the one-dimensional displacement sensor 21.

At step 705, determination is made that measurement of the thickness of the join portion 17 and its peripheral region when the rotation angle has reached a specific angle from the measurement start, and illumination of the laser by the one-dimensional displacement sensor 21 is stopped.

At step 706, the rotation section 23 is stopped with the join portion 17 and its peripheral region in a position capable of image capture by the CCD camera 22. Specifically the position capable of capture by the CCD camera 22 is a position where the join portion 17 has reached the center of a frame of the CCD camera 22.

At step 707, image capture of the join portion and the join portion vicinity is performed by the CCD camera 22, as illustrated in FIG. 6.

The image captured at step 707 of the join portion and the join portion vicinity is subjected to image processing by the camera amplifier 25. Detailed explanation of the image processing of the camera amplifier 25 is given later.

At step 708, an overall determination is made of the result of image processing by the camera amplifier 25 and the measurement result by the one-dimensional displacement sensor 21 at step 704, good/no-good determination is made of the join portion, and this result is displayed on the display device 29 of FIG. 4. Detailed explanation of the processing of step 708 is given later.

Figure 8:
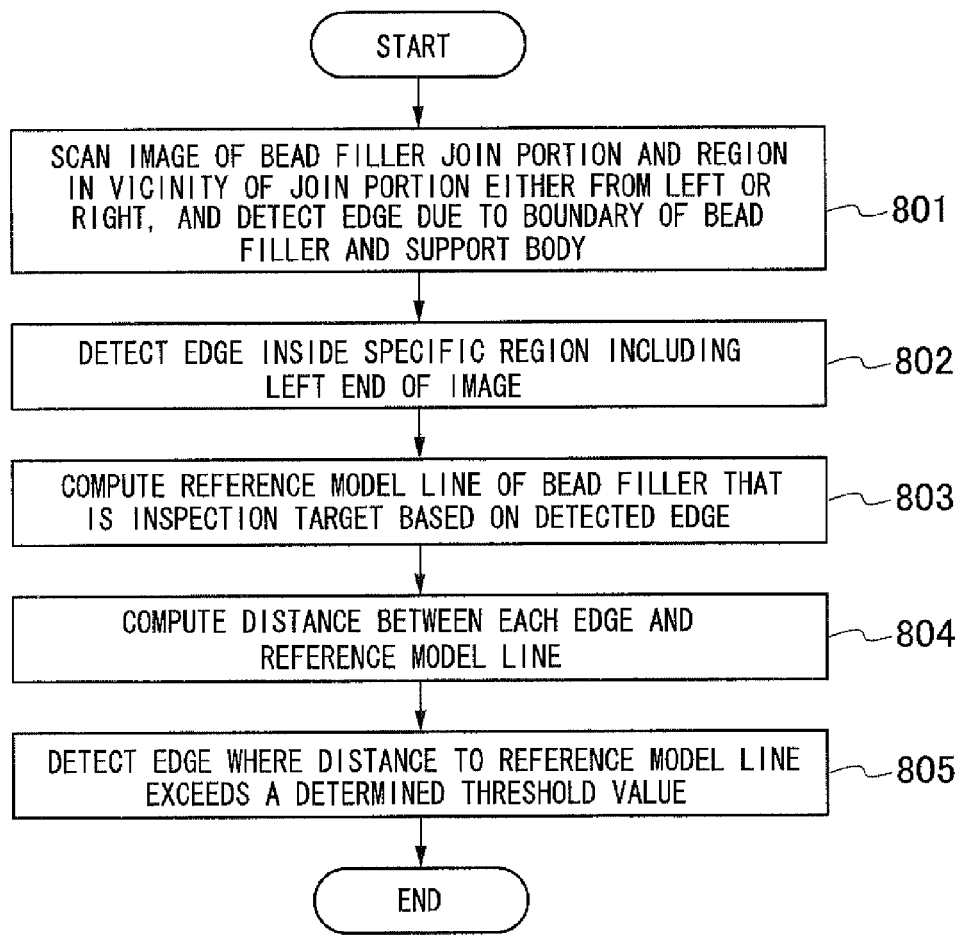
FIG. 8 is a flow chart illustrating a procedure for image processing of the first exemplary embodiment of the present invention.

Explanation next follows regarding image processing executed by the camera amplifier 25, with reference to the drawings. FIG. 8 is a flow chart illustrating an image processing sequence.

Figure 9:
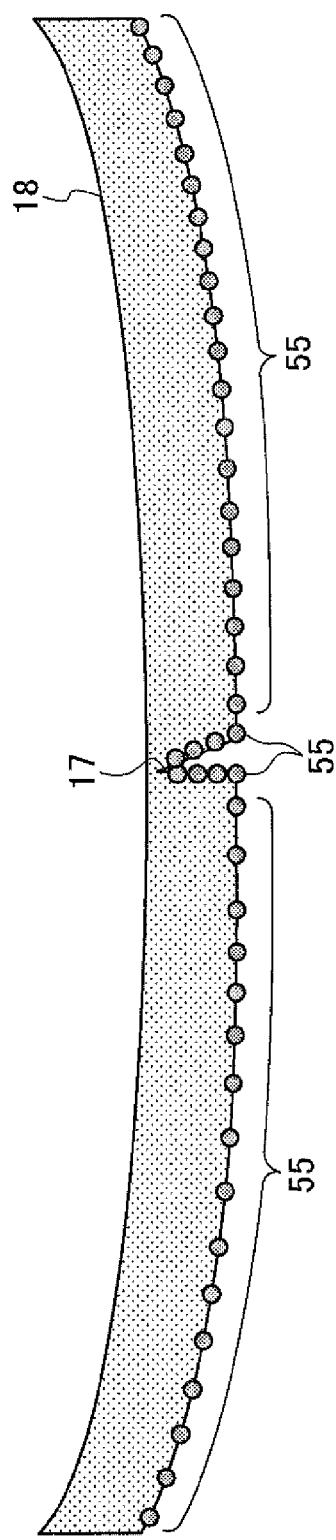
FIG. 9 is a diagram of an example of edge detection in the first exemplary embodiment of the present invention.

First, at step 801 of FIG. 8, the image of the region of the join portion and the join portion vicinity of the bead filler captured at step 707 of FIG. 7 is scanned from one end portion, the right or left, and an edge, related to the boundary of the outer edge of the bead filler and the support body on which the bead filler is mounted, is detected. An example of an edge thus detected is illustrated in FIG. 9.

As described above, the bead filler is black colored uncured rubber, and the support body is uncoated metal, and so the edge is detected by a large change in the brightness values of pixels at the boundary between the outer edge of the bead filler and the support body.

In the present exemplary embodiment, connected pixels where the difference between the brightness values of adjacent pixels exceeds a predetermined threshold value may be detected as the edge, or the edge may be detected by applying a filter to the image, such as a Sobel operator.

Figure 10:
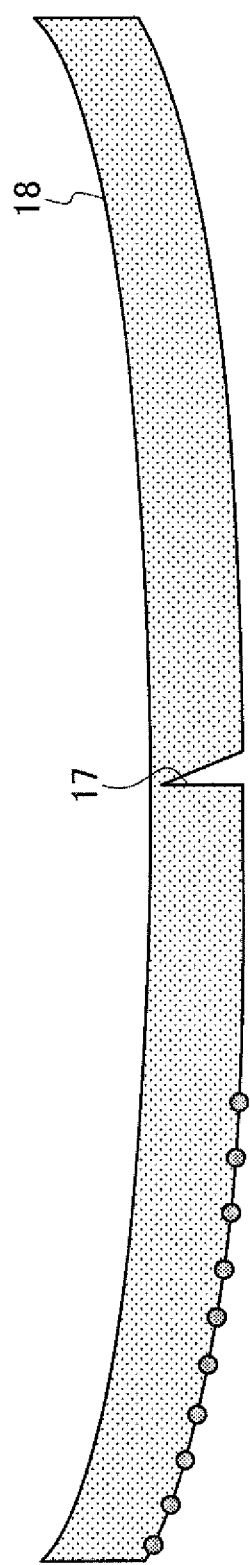
FIG. 10 is a diagram illustrating detection of an edge in a specific region including an end portion from an image in the first exemplary embodiment of the present invention.

Then, at step 802, as illustrated in FIG. 10, an edge is detected within a specific region including one end portion of the image. The specific region including one end portion of the image may be an image that has the join portion to be contained captured at the image center, and that also includes the other end portion of the image. Moreover, the specific region including one end portion or the other end portion of the image is an arbitrary range, and preferably, from the perspective of computation of a reference model line 41, as described later, includes the edge up to a position as far away as possible from one end portion or the other end portion of the image that needs to contain the join portion captured at the image center.

At step 803, the reference model line is computed to be taken as the outline portion of the bead filler inspection target based on the edge detection at step 802. Specifically, a curve is computed that passes through each position of the edge within the specific region including one end portion or the other end portion of the image, and the reference model line is computed by what is referred to as "curve fitting".

Figure 11:
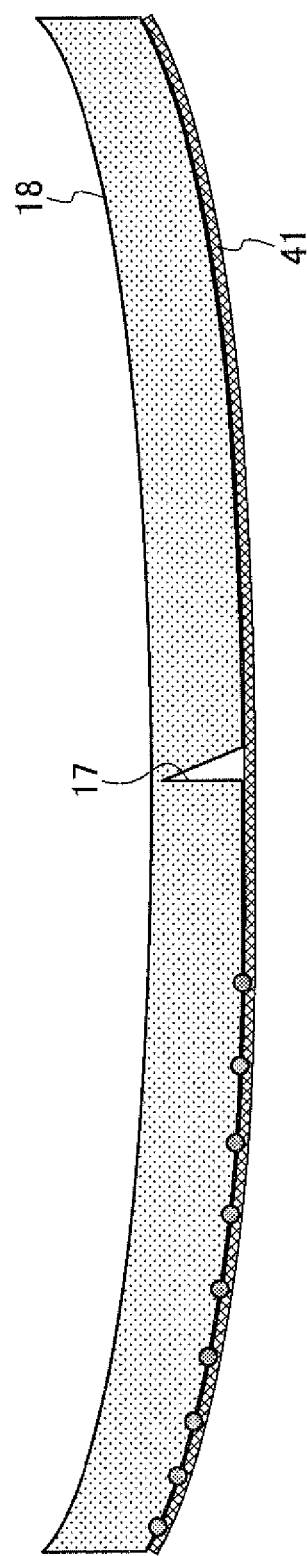
FIG. 11 is a diagram illustrating an example of curve fitting in the first exemplary embodiment of the present invention.

FIG. 11 is a diagram illustrating an example of curve fitting in the present exemplary embodiment wherein a circular arc is computed to pass through points 55 on the edge detected in the specific region at the left hand side of the image, with these taken as the reference model line 41. When capturing an image at step 707 of FIG. 7, rotation of the rotation section 23 is controlled such that the join portion 17 of the bead filler 18 is positioned at the center of the camera frame, and so the join portion is also captured at the center of the captured image. Thus by curve fitting based on the edge detected in the specific region including one end portion or the other end portion of the image, the reference model line 41 that forms the outline of the bead filler, the inspection target, can be computed without being affected by the join portion 17. Moreover, the reference model line 41 can be picked out ignoring the opening 17. In the present exemplary embodiment, the reference model line 41 can be generated by ignoring straight line portions, such as the opening 17, by reference only to locations where the edge is a free curve line.

Even when the curve is limited to a quadratic curve, it may be a circular arc, an elliptical arc, a parabolic line, or a hyperbolic line, however since the outline of bead fillers exhibit substantially circular arc shapes, in the first exemplary embodiment a circular arc is computed that matches plural points on the detected edge, and this circular arc is taken as the reference model line 41.

Next, at step 804, the distance between each point on the edge and the reference model line 41 is computed. Generally, the distance between the points and the curve is defined as a length of a line drawn from the point perpendicular to the curve, and so in the present exemplary embodiment, the length of the perpendicular line drawn from each point on the edge to the reference model line 41 is taken as the distance between each point on the edge and reference model line 41. In FIG. 11 to FIG. 14, scanning is performed from the left to the right or from the right to the left in each of the drawings, and as a result the distance of the edge to the reference model line 41 is measured. Note that distance is measured by number of pixels, however this distance may be converted into millimeter units.

At step 805, the edge is detected to include points where the distance to the reference model line 41 exceeds a predetermined threshold value, and this edge is taken as the determination target edge. The positions on the image of points on the determination target edge are also recorded, and then the image processing of the present exemplary embodiment is ended.

Figure 12:
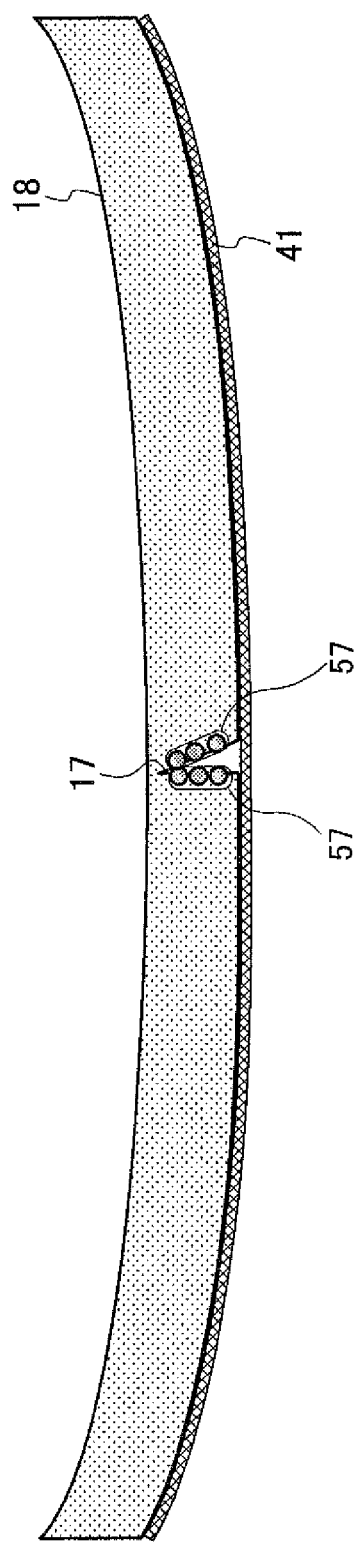
FIG. 12 is a diagram illustrating a case of "opening" in a join portion of the first exemplary embodiment of the present invention.

FIG. 12 is a diagram illustrating an example of the determination target edge is detected where the distance to the reference model line 41 exceeds the predetermined threshold value. FIG. 12 illustrates a case in which an "opening" arises in the join portion 17, and when the distance from the reference model line 41 exceeds the predetermined threshold value, the presence of edges 57 related to the join portion 17 where an "opening" has occurred are detected as determination target edges by processing of step 805. In such cases, the extension lines extending from the determination target edges intersect with the reference model line 41.

Figure 13:
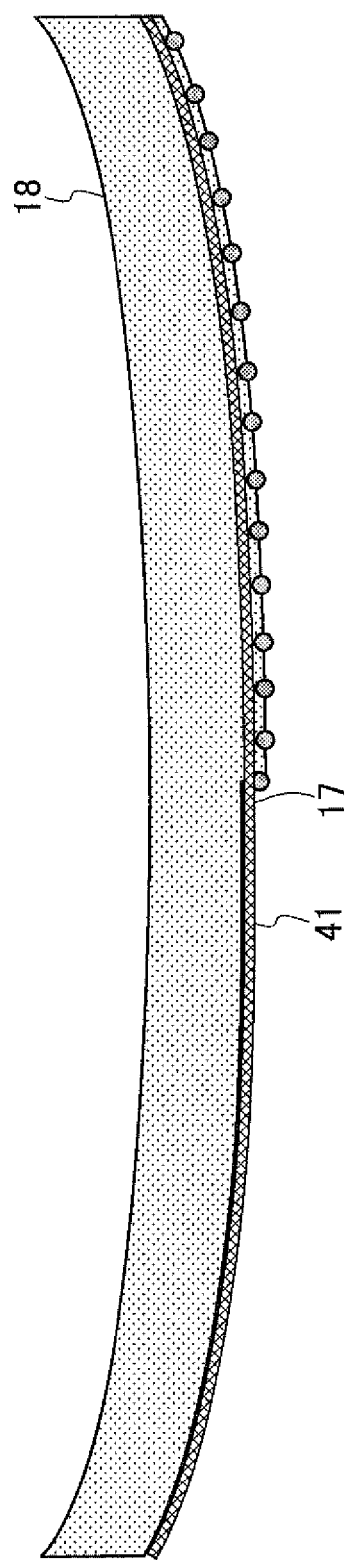
FIG. 13 is a diagram illustrating a case of "step misalignment" in a join portion of the first exemplary embodiment of the present invention.
Figure 15:
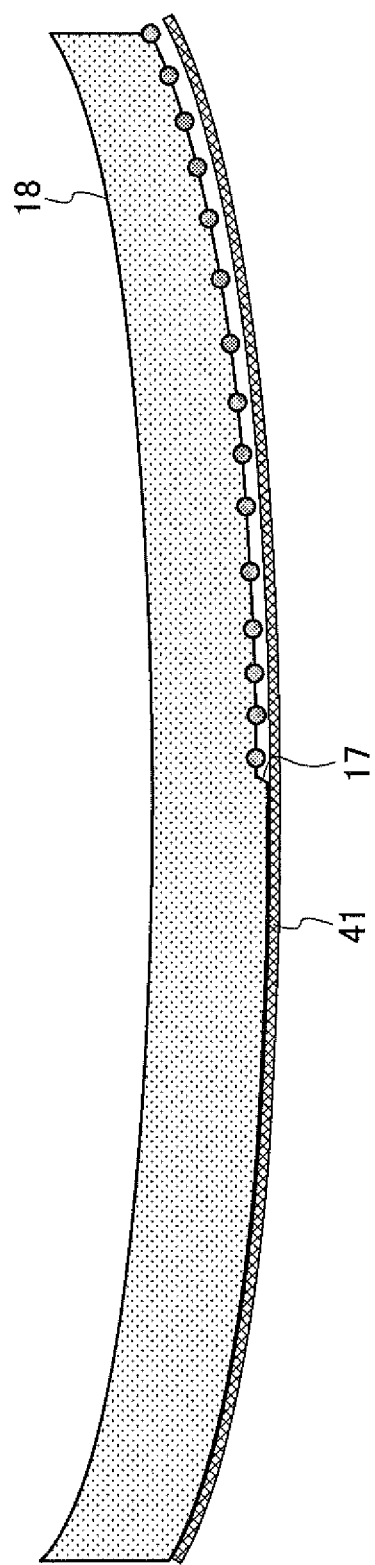
FIG. 15 is a diagram illustrating a case of "step misalignment" in a join portion of the first exemplary embodiment of the present invention.

When there is "step misalignment", as illustrated in FIG. 13 and FIG. 15, the line of a determination target edge, where the distance to the reference model line 41 exceeds the predetermined threshold value, is detected parallel to the reference model line 41. Consequently, the determination target edge and the extension line of the determination target edge do not intersect with the reference model line 41.

Figure 16:
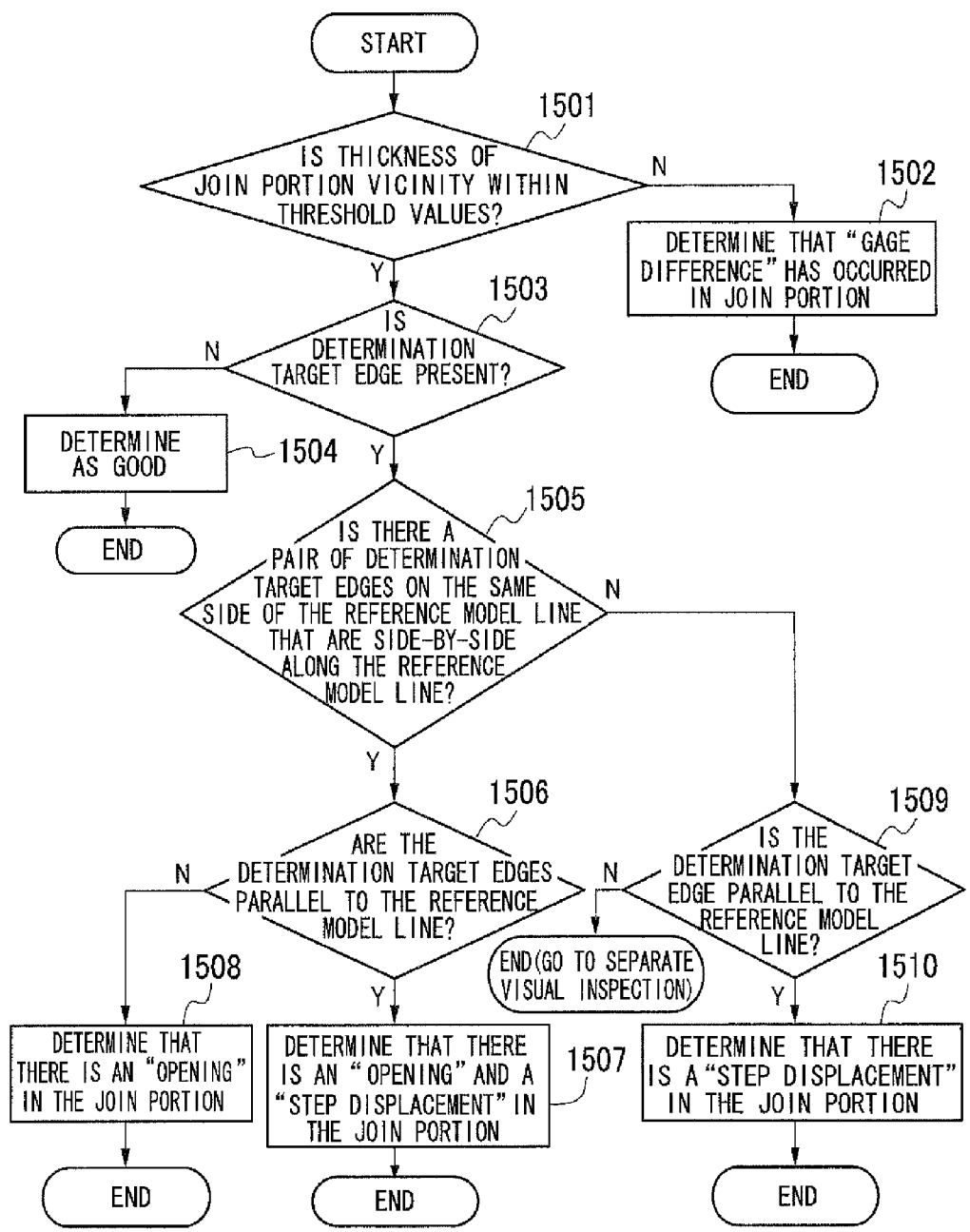
FIG. 16 is a flow chart regarding good/no-good determination of a bead filler join portion according to the first exemplary embodiment of the present invention.

Detailed explanation next follows regarding overall determination of the measurement results of the one-dimensional displacement sensor at step 704 of FIG. 7 and the image processing results, and regarding good/no-good determination processing of the bead filler join portion, with reference to FIG. 16. FIG. 16 is a flow chart regarding good/no-good determination processing of the bead filler join portion.

At step 1501, determination is made as to whether or not the thickness of the join portion vicinity measured by the one-dimensional displacement sensor at step 707 of FIG. 7 is within a predetermined threshold value.

When the thickness of the join portion vicinity is determined at step 1501 to be within the threshold value, processing proceeds to step 1503 since there is no "gage difference" present at the join portion.

When it is determined at step 1501 that the thickness of the join portion vicinity exceeds the threshold value, the occurrence of a "gage difference" is determined at step 1502, and the join portion is determined to be no-good, and processing is ended.

At the next step 1503, determination is made as to whether or not a determination target edge is present where the distance from the reference model line exceeds the predetermined threshold value, and when there is no determination target edge present, then at step 1504 the join portion of the bead filler that is the determination target is determined to be good, without defects related to "gage difference", "opening", or "step misalignment", and processing is ended.

When a determination target edge is present at step 1503, determination is then made at step 1505 as to whether or not detection has been made of a pair of determination target edges that are on the same side with respect to the reference model line 41 and are side-by-side along the reference model line 41.

When an opening occurs in the join portion, as illustrated in FIG. 12, there is a pair on the same side of the reference model line 41 and side-by-side along the direction of the reference model line 41. At step 1505, determination is made that an "opening" has occurred in the join portion in cases such as this in which a group of determination target edges are on the same side of the reference model line 41 and side-by-side along the direction of the reference model line 41.

Note that at step 1505, cases in which the group of determination target edges are on the same side of the reference model line 41 and side-by-side in the direction along the reference model line 41 may be determined by whether or not there are a pair of intersection points extension lines of the substantially segment shaped determination target edges and the reference model line present, and when there is a pair present, whether or not there is a left-right pair present of the determination target edges.

Next, at step 1506, determination is made as to whether or not the group of determination target edges are detected parallel to the reference model line 41.

When a "step misalignment" occurs at the join portion, as illustrated in FIG. 13 or FIG. 15, a determination target edge is present continuously, and the continuous determination target edge is present parallel to the reference model line 41. At step 1506, when the determination target edge is detected in this manner to be parallel to the reference model line 41, "step misalignment" is determined to have occurred at the join portion.

FIG. 13 illustrates a case where the right hand side of member 14 is misaligned downwards, the image is scanned from the left, and the reference model line 41 is computed based on the edge detected in the region of the left hand side of the image. In FIG. 13, an edge is detected parallel at the outside of the reference model line 41.

FIG. 15 illustrates a case where the left hand side of member 14 is misaligned downwards, the image is scanned from the left, and the reference model line 41 is computed based on the edge detected in the region of the left hand side of the image. In FIG. 15, an edge is detected parallel to and at the inside of the reference model line 41.

Note that at step 1506, determination that "step misalignment" has occurred when the determination target edge is detected to be parallel to the reference model line 41 may be determined by determining whether or not the determination target edge and the extension line of the determination target edge intersect with the reference model line 41, with determination that a "step misalignment" has occurred made when they do not intersect.

Figure 14:
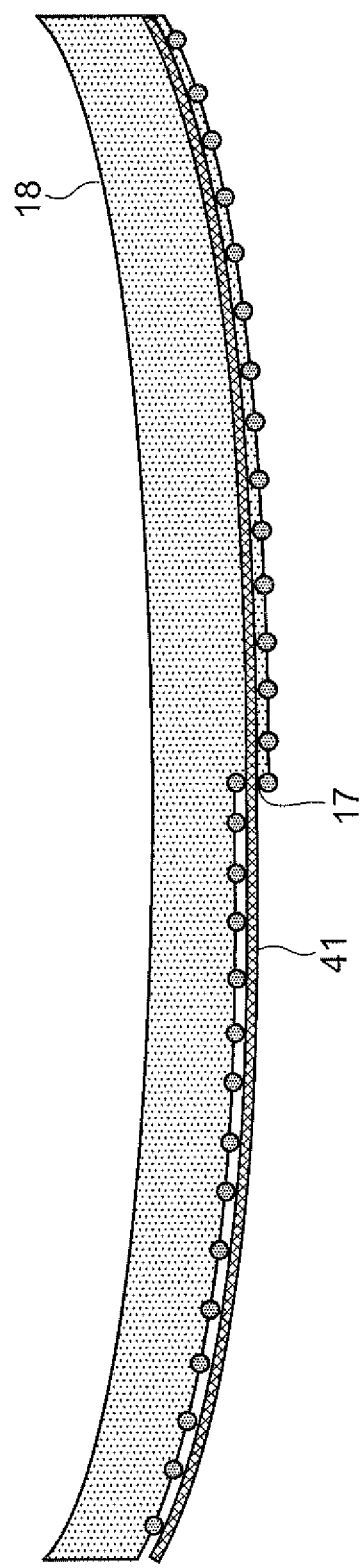
FIG. 14 is a diagram illustrating a case of "step misalignment" in a join portion of the first exemplary embodiment of the present invention.

Or, when the reference model line 41 is detected from the edge, as illustrated in FIG. 14, a reference model line 41 may be obtained in a state in which a step misalignment portion and the reference model line 41 intersect, and the distance between the obtained reference model line 41 and the edge measured.

In measurement of the distance between the above edge and the reference model line 41, in cases in which the positional relationship changes between the edge and the reference model line 41, namely at a place in FIG. 14 where there is a change from the state (A) of the edge on the left hand side the reference model line 41 to the state (B) of the edge on the right hand side of the reference model line 41, this is the place where there is a step misalignment. Therefore, the maximum values of the distance between the edge and the reference model line 41 in A and B are added together, and the summed values compared with a predetermined threshold value. Good/no-good determination is made of the step misalignment thereby. In the present exemplary embodiment, FIG. 14 illustrates a case where there is a change from the state (A) of the edge on the left hand side of the reference model line 41 to the state (B) of the edge on the right hand side of the reference model line 41, and the position where each of the edges are side-by-side illustrates where there is a change to invert with respect to the reference model line 41, and the distances between the edges and the reference model line 41 are measured in a specific region including the portion where such a change occurs. The specific region is a region of the portion where such a change occurs and a region in the vicinity thereof, however it preferably has a surface area such that plural distances between the edge and the reference model line 41 can be measured, so as to enable the maximum value of the distance between the edge and the reference model line 41 to be extracted.

When a determination target edge parallel to the reference model line 41 is detected at step 1506, determination is made at step 1507 that both an "opening" and a "step misalignment" have occurred at the join portion, and processing is ended.

When a determination target edge parallel to the reference model line 41 is not detected at step 1506, determination is made at step 1508 that an "opening" has occurred at the join portion, and processing is ended.

When the determination target edges are detected at step 1505 to be on the same side with respect to the reference model line 41 and side-by-side in a direction along the reference model line 41, determination is made at step 1509 as to whether or not the determination target edges are parallel to the reference model line 41.

When the determination target edges are detected at step 1509 to be parallel to the reference model line 41, then determination is made at step 1510 that a "step misalignment" has occurred at the join portion and processing is ended. At step 1509, it is considered that noise or the like in the images has been detected as an edge when the determination target edges are not detected to be parallel to the reference model line 41, the processing is ended, and visual inspection is performed by a different operator.

Note that the determination result of the processing according to FIG. 16 may be displayed on the display device 29 illustrated in FIG. 4.

According to the first exemplary embodiment, the difference in brightness between the pixels related to the bead filler and the pixels related to the support body is large, and an edge at a boundary of an outer edge of the bead filler and the support body can be easily detected, and so the join portion can be determined to be no-good when there is an edge present that departs from the reference model line computed based on the edge of a region of the detected edge not containing the join portion.

Second Exemplary Embodiment

Explanation next follows regarding a second exemplary embodiment. The image processing in the second exemplary embodiment is different from that of the first exemplary embodiment, and so explanation is omitted of portions that are similar, and explanation follows regarding portions that differ. Note that detection of "gage difference" is similar to that of the first exemplary embodiment.

In the image processing of the second exemplary embodiment, an image captured by a CCD camera 22 is divided into "segments" that are minimum units of a region for detecting the edge, and "opening" or "step misalignment" in the join portion of the member 14 is detected by detecting the presence or absence of edges where there is a large change in brightness values on scanning each of the divided "segments" in a specified direction.

Figure 17:
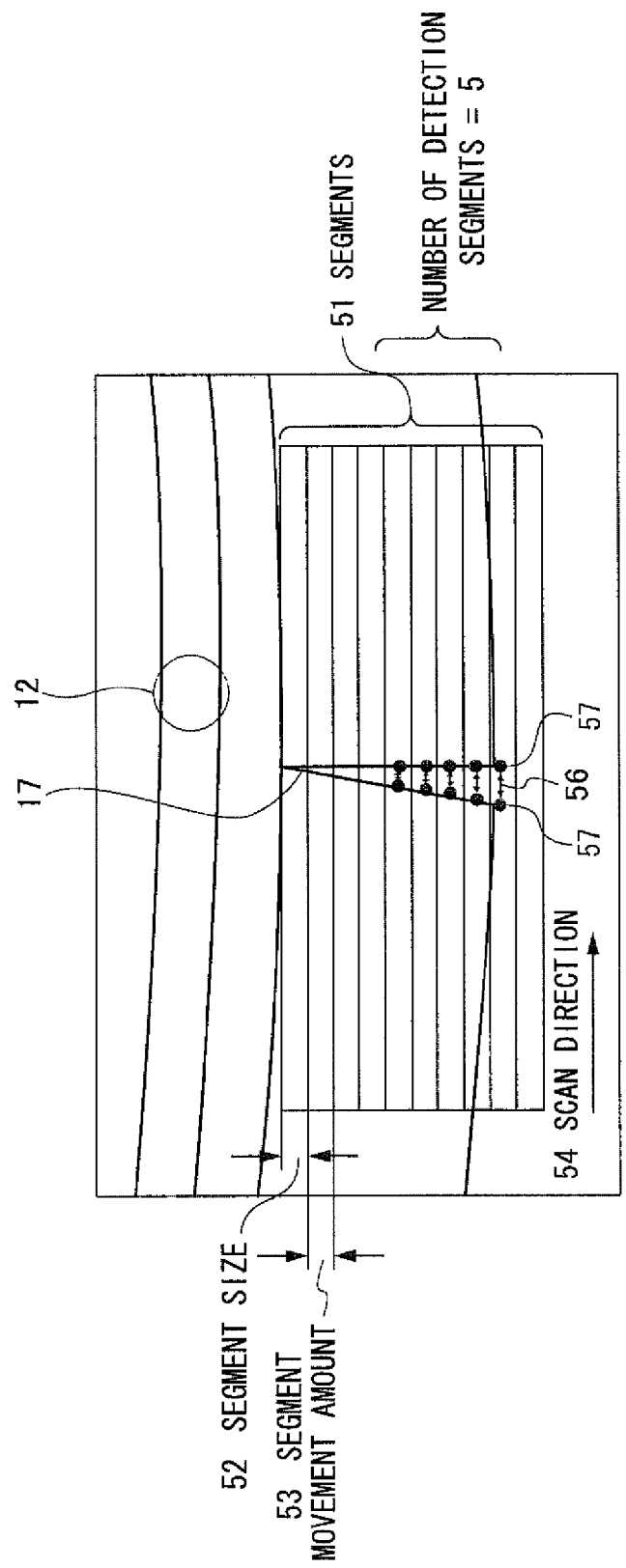
FIG. 17 is a diagram illustrating an example of region specification according to a second exemplary embodiment of the present invention.

As illustrated in FIG. 17, segments 51 that are minimum units of a region for detecting the edge are rectangular regions elongated along the left-right, namely along the support body rotation direction.

In the second exemplary embodiment, out of the images captured by the CCD camera 22 illustrated in FIG. 4, a rectangle measurement region is specified from the PLC 27 illustrated in FIG. 4 to the camera amplifier 25 as a region for performing image processing. A segment size 52 that is the width of the segments 51 is also specified from the PLC 27 to the camera amplifier 25, a segment movement amount 53 that is the interval between each segment is also specified, and the portions of the measurement region are automatically divided up as portions of the measurement region as illustrated in FIG. 17.

The segment size 52 is an arbitrary size, but is preferably from about 1 to several pixels in order to perform precise determination. The length of the segments is also arbitrary, and may be made a value that is longer than the length of the join portion.

In specifying the measurement region as described above, as illustrated in FIG. 17, specification may be made such that the outer edge of the bead filler is always included therein, however specification is made such that bead core 12 wound with cover tape is not included. Sometimes with cover tape covering the surface of a bead core, components of compounds of rubber stand out in white relief, and this is sometimes misdetected as an edge. Moreover, "opening" and "step misalignment" defects in join portions tend to occur in the vicinity of the outer edge of the bead filler rather than in the vicinity of the bead core.

The above specification of measurement region and division of measurement region into the segments 51 is the same for both detection of "opening" and detection of "step misalignment". In the second exemplary embodiment, each segment of the measurement region is scanned to detect for "opening", and then the measurement region is scanned one more time for each of the segments to detect for "step misalignment".

Details regarding detection of "opening" and "step misalignment" in the second exemplary embodiment are given below.

In the second exemplary embodiment, "opening" in the join portion of the member 14 is detected for by scanning each of the segments 51 according the scan direction 54 of FIG. 17.

The segments 51 illustrated in FIG. 17 are scanned from the left hand side, and a first edge is detected at a location where blackish, low brightness pixels due to rubber change to whitish, high brightness pixels due to uncoated metal, and then when the segments are scanned again, a second edge is detected at a location where whitish, high brightness pixels due to uncoated metal change to blackish, low brightness pixels due to rubber.

Note that in the second exemplary embodiment, pixels are scanned within the segments 51, and so pixels configuring the edges present within the segments 51 are detected. In the second exemplary embodiment, the groups of pixels detected as pixels configuring the edges are treated as being those of a single edge.

The accordingly means that when an "opening" occurs in a join portion, as illustrated in FIG. 17, there are always two edges 57 present within a given segment, namely a pair of edges 57. Note that the scanning direction may be from left to right as in FIG. 17, or from right to left.

Such segments that have a pair of edges are treated as being segments related to an "opening", and the number of individual segments with a pair of edges within the measurement region are measured. In the second exemplary embodiment, the detected number of segments, this being the number of individual segments having a pair of edges within the measurement region, is taken as the height of the "opening".

In detection of "opening" in the second exemplary embodiment, a threshold value is provided for the number of detected segments in the image measurement region, and determination is made that an "opening" has not occurred in the bead filler corresponding to the image when the number of detected segments is less than the threshold value.

Figure 18:
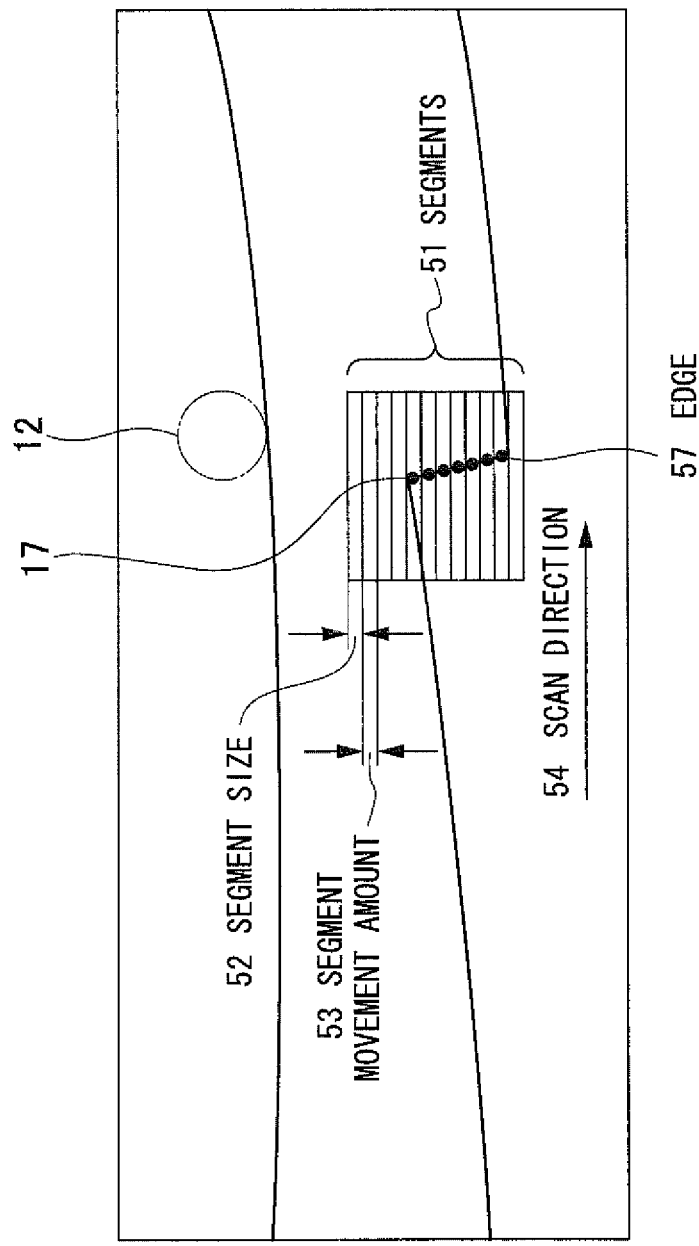
FIG. 18 is a diagram illustrating an example of region specification according to the second exemplary embodiment of the present invention.

In the second exemplary embodiment, detection is made for "step misalignments" in the join portion of the member 14 by scanning each of the segments 51 illustrated in FIG. 18.

Figure 19:
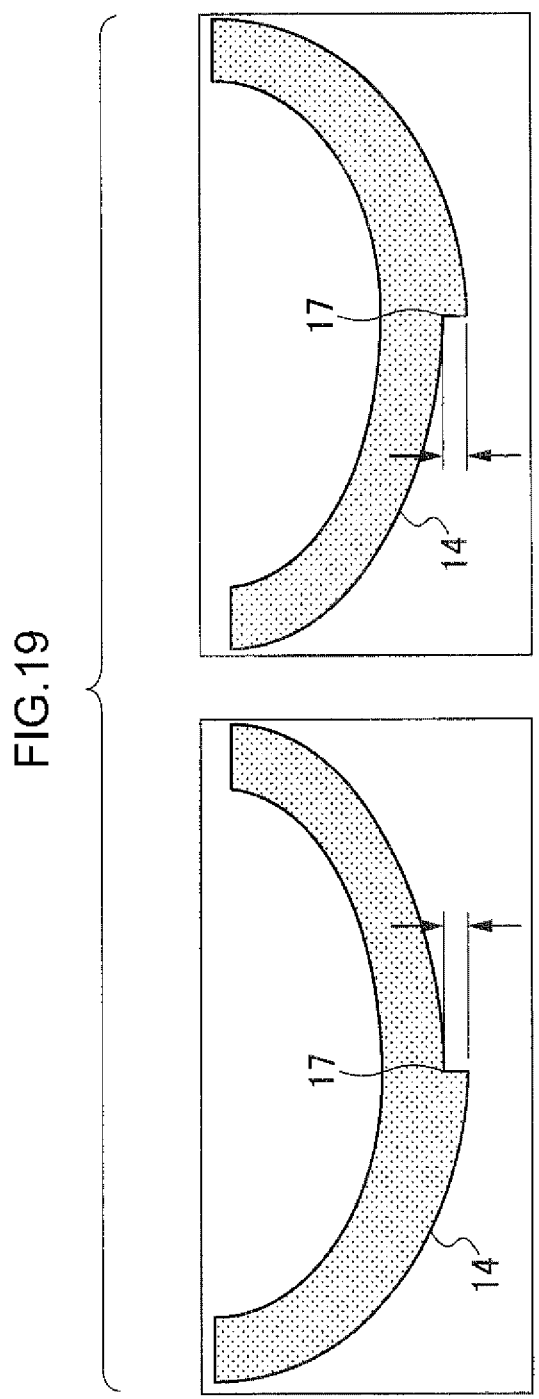
FIG. 19 is a diagram illustrating cases of "step misalignment" to be detected in the second exemplary embodiment of the present invention.

Detection of "step misalignments" is also, similar to when detection for "openings" is made as described above, by scanning segments, and detecting each edge at locations where the blackish, low brightness pixels due to rubber change to the whitish, high brightness pixels due to uncoated metal, or each edge at locations where the whitish, high brightness pixels due to uncoated metal change to blackish, low brightness pixels due to rubber. Namely, as illustrated in FIG. 18, edges 57 are detected to be present within the segments. With a "step misalignment", in both cases in which the left hand side of the end of the member 14 illustrated on the left of FIG. 19 is misaligned downwards, and cases in which the right hand side of the end of the member 14 illustrated on the right of FIG. 19 is misaligned downwards, there is a single edge detected within a single segment.

Each of the segments in FIG. 18 is scanned from left to right according to the scan direction 54, however since the right hand side of the end of the member 14 is misaligned downwards, an edge is detected at a location where the whitish, high brightness pixels due to uncoated metal change to the blackish, low brightness pixels due to rubber.

When the left hand side of the end of the member 14 is misaligned downwards, in contrast to in FIG. 18, edges are detected where the blackish, low brightness pixels due to rubber change to whitish, high brightness pixels due to uncoated metal when each of the segments are scanned from left to right.

In the second exemplary embodiment, a segment with a single edge is treated as being a segment related to "step misalignment", and the number of individual segments with a single edge within the measurement region is measured. In the second exemplary embodiment, the number of individual segments with a single edge in the measurement region is taken as the number of detected segments, and the number of detected segments is taken as the height of the "step misalignment".

In "step misalignment" detection of the second exemplary embodiment, a threshold value is provided for the number of detected segments in the measurement region of the image, and "step misalignment" is determined not to have occurred in the bead filler corresponding to the image when the number of detected segments is less than the threshold value.

Figure 20:
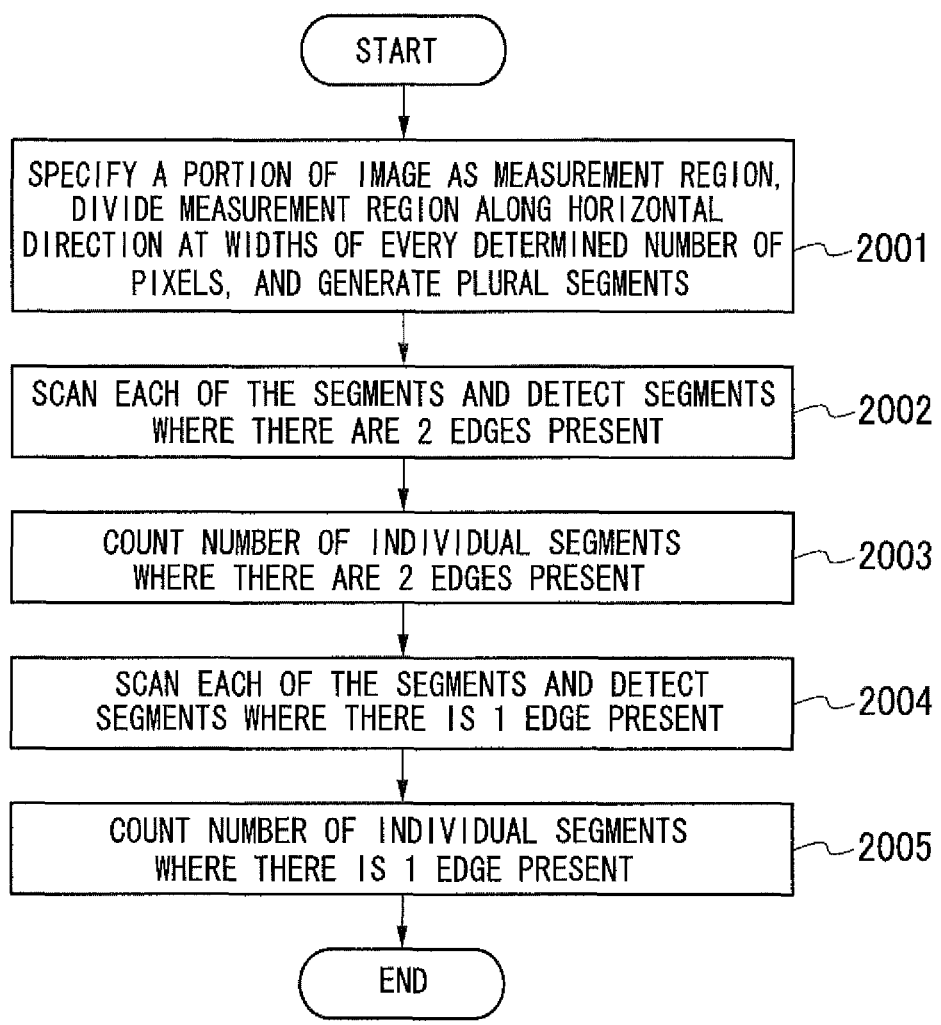
FIG. 20 is a flow chart illustrating a case of an example of a procedure of image processing of the second exemplary embodiment of the present invention.

Based on the description above, explanation next follows regarding flow of image processing executed by the camera amplifier in the second exemplary embodiment, with reference to FIG. 20. The flow chart in FIG. 20 illustrates a sequence of image processing in the second exemplary embodiment.

First, at step 2001, a portion of the image is specified as the measurement region, and plural segments are generated by dividing the measurement region in the horizontal direction at each width of a predetermined number of pixels.

At step 2002, each of the segments is scanned and detection is made for segments having a pair of edges, and the number of individual segments having a pair of edges is measured at step 2003.

Determination is made of the presence or absence of an "opening" in the join portion by determination of the good/no-good determination processing at step 709 of FIG. 7, described later, of whether or not the number of individual segments having a pair of edges is within a predetermined threshold value.

At step 2004, each of the segments is scanned again and detection is made for segments having a single edge, and the number of individual segments having a single edge is measured at step 2005.

Determination is made of the presence or absence of an "opening" in the join portion by determination of the good/no-good determination processing at step 709 of FIG. 7, described later, of whether or not the number of individual segments having a single edge is within a predetermined threshold value.

The image processing of the second exemplary embodiment is ended after measuring the number of individual segments with a single edge at step 2005.

Note that the procedures for detecting "opening" and the procedure for detecting "step misalignment" in FIG. 20 may be performed in the reverse sequence. Specifically, detection of edges related to "step misalignment" may be performed in step 2002 and step 2003, and the detection of edges related to "opening" may be performed in step 2004 and step 2005.

Explanation next follows regarding processing for overall determination of the measurement results of the one-dimensional displacement sensor at step 709 of FIG. 7 and the results of image processing of the second exemplary embodiment, and for performing good/no-good determination of the bead filler join portion, with reference to FIG. 21. FIG. 21 is a flow chart illustrating good/no-good determination of the bead filler join portion according to the first exemplary embodiment.

At step 2101, determination is made as to whether or not the thickness of the join portion vicinity measured by the one-dimensional displacement sensor at step 704 of FIG. 7 is within the predetermined threshold value.

Processing proceeds to step 2103 when the thickness of the join portion vicinity is within the threshold value at step 2101, since no "gage difference" has occurred in the join portion.

When the thickness of the join portion vicinity has exceeded the threshold value at step 2101, determination is made at step 2102 that "gage difference" has occurred in the join portion, and processing is ended.

Next at step 2103, determination is made as to whether or not the number of individual segments having a pair of edges is within the threshold value.

When the number of individual segments having a pair of edges is within the threshold value, determination is made at step 2104 as to whether or not the number of individual segments having a single edge is within a threshold value.

When the number of individual segments having a single edge is within the threshold value, determination is made at step 2105 that there is no defect related to an "opening" or a "step misalignment" in the join portion of the bead filler that is subject to investigation, and then processing is ended.

When the number of individual segments having a single edge is not within the threshold value at step 2104, determination is made at step 2106 that "step misalignment" has occurred in the join portion of the bead filler that is subject to investigation, and the processing is ended.

Moreover, when the number of individual segments having a pair of edges is not within the threshold value at step 2103, determination is made at step 2107 as to whether or not the number of individual segments having a single edge is within a threshold value.

When at step 2107 the number of individual segments having a single edge is within the threshold value, determination is made at step 2108 that an "opening" has occurred in the join portion of the bead filler that is subject to investigation, and the processing is ended.

When at step 2107 the number of individual segments having a single edge is not within the threshold value, determination is made at step 2109 that an "opening" and a "step misalignment" has occurred in the join portion of the bead filler that is subject to investigation, and the processing is ended.

The determination result of processing according to FIG. 21 may be displayed on the display device 29 illustrated in FIG. 4.

Note that in the second exemplary embodiment, after the image has been divided into plural segments, edges are detected for in each of the segments, and the number of individual pixel groups configuring the detected edges is computed for each of the segments. However configuration may be made such that after first detecting for edges in the image overall, the image is divided into plural segments, and then the individual number of pixels of groups configuring edges is computed for each of the segments.

The following types of filter may be employed in the second exemplary embodiment.

(1) Erode Filter

An effective method for removing white noise components is to replace the brightness value of the central pixel out of a 3×3 pattern with the minimum brightness value out of 9 pixels (including the central pixel) of a 3×3 pattern. This is employed in the second exemplary embodiment in order to remove white points that would be detected as edges.

(2) Dilate Filter

An effective method for removing black noise components is to replace the brightness value of the central pixel out of a 3×3 pattern with the maximum brightness value out of 9 pixels (including the central pixel) of a 3×3 pattern. This is employed in the second exemplary embodiment in order to remove black points that would be detected as edges.

(3) Smoothing Filter

An effective method for removing noise is to replace the brightness value of the central pixel out of a 3×3 pattern with the average brightness value out of 9 pixels (including the central pixel) of a 3×3 pattern.

(4) Binarization Filter

Each pixel in an image is classified either as a white pixel or a black pixel using a specific brightness as a threshold value. An image with sharp black-white contrast is obtained with such a binarization filter, enabling false edge detection to be reduced.

INDUSTRIAL APPLICABILITY

As described above, the present invention enables high precision automatic good/no-good determination of join portions of bead fillers that previously relied on visual inspection by inspectors, thereby enabling a reduction in effort and increase in efficiency to be achieved in the process.

Moreover it can be said that, by high precision automatic good/no-good determination of the join portions of bead fillers, determination mistakes due to inattention of inspectors can be prevented, thereby enabling an improvement in product quality to be achieved.

The entire specification of Japanese patent application number 2011-158921 is incorporated in the present specification by reference.

All cited documents, patent applications and technical standards mentioned in the present specification are incorporated by reference in the present specification to the same extent as if the individual cited document, patent application, or technical standard was specifically and individually indicated to be incorporated by reference.

The invention claimed is:

1. A bead filler inspection apparatus comprising:
   an imaging section that captures an image of a join portion of a bead filler formed by being wound onto a rotating support body and joined, and a region containing a boundary between an outer edge of the bead filler and the support body;
   an edge detection section that detects an edge corresponding to the boundary between the outer edge of the bead filler and the support body based on an image obtained by the imaging section;
   a computation section that computes distances between a reference model line, that runs along the rotation direction of the support body and is determined based on an edge detected by the edge detection section, and each respective point on the edge present in a region containing the join portion; and
   a determination section that performs good/no-good determination on the join portion based on the distances.

2. The bead filler inspection apparatus of claim 1, wherein:
   the determination section determines that there is an opening in the bead filler join portion when there is a pair of left-right determination target edges present where the distance between the reference model line and each of the respective points on an edge present in the region containing the join portion exceeds a predetermined distance threshold value.

3. The bead filler inspection apparatus of claim 1, wherein:
   the determination section determines that one end of a member for forming the bead filler is misaligned in a width direction with respect to the other end of the member at the bead filler join portion when the determination target edge and the reference model line do not intersect with each other.

4. A bead filler inspection program that causes a non-transitory computer-readable medium to function as:
   an edge detection section that, based on an image captured by an imaging section that captures an image of a join portion of a bead filler formed by being wound onto a rotating support body and joined and a region containing a boundary between an outer edge of the bead filler and the support body, detects an edge corresponding to the boundary between the outer edge of the bead filler and the support body;
   a computation section that computes distances between a reference model line, that runs along the rotation direction of the support body and is determined based on an edge detected by the edge detection section, and each respective point on the edge present in a region containing the join portion; and
   a determination section that performs good/no-good determination on the join portion based on the distances.

5. A bead filler inspection method that comprises:
   a step for image capturing that captures an image of a join portion of a bead filler formed by being wound onto a rotating support body and joined, and a region containing a boundary between an outer edge of the bead filler and the support body;
   a step for edge detecting that detects an edge corresponding to the boundary between the outer edge of the bead filler and the support body based on an image obtained by imaging during image capturing;
   a step for computing that computes distances between a reference model line, that runs along the rotation direction of the support body and is determined based on an edge detected by the edge detecting, and each respective point on the edge present in a region containing the join portion; and
   a step for determining that performs good/no-good determination on the join portion based on the distances.

* * * * *